United States Patent
Swanson et al.

(10) Patent No.: US 8,612,261 B1
(45) Date of Patent: Dec. 17, 2013

(54) AUTOMATED LEARNING FOR MEDICAL DATA PROCESSING SYSTEM

(71) Applicant: Health Management Associates, Inc., Naples, FL (US)

(72) Inventors: Brian S. Swanson, Petaluma, CA (US); Kenneth R. Chatfield, Naples, FL (US); Christopher B. Smith, Naples, FL (US)

(73) Assignee: Health Management Associates, Inc., Naples, FL (US)

( * ) Notice: Subject to any disclaimer, the term of this patent is extended or adjusted under 35 U.S.C. 154(b) by 0 days.

(21) Appl. No.: 13/717,469

(22) Filed: Dec. 17, 2012

Related U.S. Application Data

(63) Continuation-in-part of application No. 13/599,601, filed on Aug. 30, 2012.

(60) Provisional application No. 61/649,522, filed on May 21, 2012.

(51) Int. Cl.
*G06F 19/00* (2011.01)

(52) U.S. Cl.
USPC ............................................................ 705/3

(58) Field of Classification Search
USPC .......................................... 705/3, 34; 704/9
See application file for complete search history.

(56) References Cited

U.S. PATENT DOCUMENTS

| | | | |
|---|---|---|---|
| 6,283,761 B1 | 9/2001 | Joao | |
| 6,684,188 B1 | 1/2004 | Mitchell et al. | |
| 6,915,254 B1 * | 7/2005 | Heinze et al. | 704/9 |
| 7,233,938 B2 | 6/2007 | Carus et al. | |
| 7,379,946 B2 | 5/2008 | Carus et al. | |
| 7,584,103 B2 | 9/2009 | Fritsch et al. | |
| 7,613,610 B1 | 11/2009 | Zimmerman et al. | |
| 7,689,544 B2 | 3/2010 | Koenig | |
| 7,822,598 B2 | 10/2010 | Carus et al. | |
| 8,095,544 B2 | 1/2012 | Boone et al. | |
| 8,311,848 B2 | 11/2012 | Subash et al. | |
| 2002/0004727 A1 | 1/2002 | Knaus et al. | |
| 2002/0010679 A1 | 1/2002 | Felsher | |
| 2002/0194026 A1 | 12/2002 | Klein et al. | |
| 2003/0105638 A1 | 6/2003 | Taira | |

(Continued)

OTHER PUBLICATIONS

Non-Final Office Action dated Dec. 26, 2012, mailed in related U.S. Appl. No. 13/599,601, 16 pages.

(Continued)

*Primary Examiner* — John Pauls
(74) *Attorney, Agent, or Firm* — Terrile, Cannatti, Chambers & Holland, LLP; Kent B. Chambers

(57) ABSTRACT

In at least one embodiment, an automated medical data machine learning system and method allow a natural language processing ("NLP") system to automatically learn via, for example, feedback to improve ongoing performance of the natural language processing system. The particular technology for improving the interpretation by the NLP system of future input data is a matter of design choice. In at least one embodiment, the automated medical data learning system and method includes a linguistics module that determines the part of speech of a particular term or term, such as use as a noun or verb. In at least one embodiment, the system and method learns an interpretation based on a source of the input data. In at least one embodiment, the system and method includes a statistics module that allows the system and method to determine a most probable interpretation or multiple interpretations.

27 Claims, 11 Drawing Sheets

(56) References Cited

U.S. PATENT DOCUMENTS

| | | |
|---|---|---|
| 2003/0144886 A1 | 7/2003 | Taira |
| 2003/0212544 A1* | 11/2003 | Acero et al. .................. 704/9 |
| 2003/0233252 A1 | 12/2003 | Haskell et al. |
| 2005/0137910 A1 | 6/2005 | Rao et al. |
| 2006/0020492 A1 | 1/2006 | Cousineau et al. |
| 2006/0020493 A1 | 1/2006 | Cousineau et al. |
| 2006/0026003 A1 | 2/2006 | Carus et al. |
| 2007/0112599 A1 | 5/2007 | Liu et al. |
| 2007/0168382 A1 | 7/2007 | Tillberg et al. |
| 2007/0192143 A1 | 8/2007 | Krishnan et al. |
| 2008/0059224 A1 | 3/2008 | Schechter |
| 2008/0255884 A1* | 10/2008 | Carus et al. .................. 705/3 |
| 2010/0138239 A1 | 6/2010 | Reicher et al. |
| 2010/0138241 A1 | 6/2010 | Ruark et al. |
| 2011/0119089 A1 | 5/2011 | Carlisle |
| 2011/0213625 A1 | 9/2011 | Joao |
| 2011/0276346 A1 | 11/2011 | Reiner |
| 2011/0282687 A1 | 11/2011 | Koll |
| 2012/0078763 A1* | 3/2012 | Koll et al. .................. 705/34 |
| 2012/0209626 A1 | 8/2012 | Carus et al. |
| 2012/0215551 A1 | 8/2012 | Flanagan et al. |
| 2012/0232923 A1 | 9/2012 | Carus et al. |

OTHER PUBLICATIONS

Response to Non-Final Office Action dated Dec. 26, 2012, as filed in related U.S. Appl. No. 13/599,601 on Mar. 26, 2013, 22 pages.

Final Office Action dated Jun. 14, 2013, mailed in related U.S. Appl. No. 13/599,601, 16 pages.

* cited by examiner

| DICTATED TEXT FROM CLINICIAN 804 | AUTOMATED DECISION 806 | CLINICIAN FEEDBACK 808 | FINAL DECISION 810 |
|---|---|---|---|
| DIAGNOSIS IS CHRONIC RENAL INSUFFICIENCY | DIAGNOSIS: CHRONIC KIDNEY DISEASE (CKD) | POSITIVE FEEDBACK FOR USING "CHRONIC KIDNEY DISEASE (CKD)" IN PLACE OF "CHRONIC RENAL INSUFFICIENCY | DIAGNOSIS: CHRONIC KIDNEY DISEASE (CKD) |
| PATIENT ADMITS TO USING SNUS 8 TO 10 PACKETS A DAY | TOBACCO USE: NEGATIVE | "SNUS" IS POSITIVE INDICATOR FOR TOBACCO USE | TOBACCO USE: POSITIVE |
| PATIENT PRESENTS WITH ALBUMIN 3.0, UNDERWEIGHT | HISTORY OF PRESENT ILLNESS: SEVERE MALNUTRITION | NEGATIVE FEEDBACK FOR ALBUMIN 3.0 INDICATING SEVERE MALNUTRITION | HISTORY OF PRESENT ILLNESS: MODERATE MALNUTRITION |

FIGURE 8

AUTOMATED LEARNING FOR MEDICAL DATA PROCESSING SYSTEM

CROSS-REFERENCE TO RELATED APPLICATION

This application claims the benefit under 35 U.S.C. §119(e) of U.S. Provisional Application No. 61/649,522, filed May 21, 2012, and entitled "Medical Record Generation and Processing." U.S. Provisional Application No. 61/649,522 includes exemplary systems and methods and is incorporated by reference in its entirety.

This application is a continuation in part of U.S. patent application Ser. No. 13/599,601, filed Aug. 30, 2012, and entitled "Medical Record Generation and Processing", which claims priority under 35 U.S.C. §119(e) to U.S. Provisional Application No. 61/649,522. U.S. patent application Ser. No. 13/599,601 includes exemplary systems and methods and is incorporated by reference in its entirety.

BACKGROUND OF THE INVENTION

1. Field of the Invention

The present invention relates in general to the field of electronics, and more specifically to a system and method for automated learning and medical data processing.

2. Description of the Related Art

Medical records often include patient information and a history of patient examinations, orders, and recommended treatment plans. Medical treatment facilities, such as hospitals, clinics, and physician offices, utilize the medical records for a variety of purposes. Such purposes include providing historical reference data that is useful for patient follow-up and subsequent examinations and treatment. Additionally, the medical records provide a basis for invoicing and compensation for medical services rendered. Additionally, medical records can provide data useful in measuring the historical quality of a particular treatment facility and/or treating clinician. The term "clinician" as used herein is a generic term representing any health care provider including physicians, physician assistants, nurses, medical lap technicians, psychologists, and physical therapists.

FIG. 1A depicts a medical record storage system and process 100. The medical record storage system and process 100 stores medical records 105 in a database of a medical record storage server 103 for subsequent access and processing. Clinicians examine a patient and record medical history data regarding the patient, the examination, and a recommended treatment. The medical data is recorded by personnel 102, submitted to the medical record storage server 103, and stored as electronic medical records 105. The method of electronic recordation is generally transcription of hand-written notes 104, direct entry 106 into a computer using, for example, a keyboard or voice recognition technology, or scanned 108. The medical records 105 are stored as images, such as portable document files (PDF) or other image format types. Government regulations can encourage the creation of electronic medical records by providing financial incentives for the creation of electronic medical records or penalties for failing to create electronic medical records.

The medical records 105 are generally coded in accordance with medical classifications in accordance with a standard set of medical record codes such as the International Statistical Classification of Diseases and Related Health Problems (most commonly known by the abbreviation ICD). The ICD is a medical classification that provides codes to classify diseases and a wide variety of signs, symptoms, abnormal findings, complaints, social circumstances, and external causes of injury or disease. Under this system, every health condition can be assigned to a unique category and given a code, up to six characters long. Such categories can include a set of similar diseases. The ICD is published by the World Health Organization (WHO) and used worldwide for morbidity and mortality statistics, reimbursement systems, and automated decision support in medicine. The ICD coding system is designed to promote international comparability in the collection, processing, classification, and presentation of these statistics.

In addition to ICD, additional medical record codes include the Current Procedural Terminology (CPT) code set, which is maintained by the American Medical Association through the CPT Editorial Panel. The CPT code set describes medical, surgical, and diagnostic services and is designed to communicate uniform information about medical services and procedures among physicians, coders, patients, accreditation organizations, and payers for administrative, financial, and analytical purposes.

To code the medical records 105 in accordance with the current ICD, human coders utilize a coding system 112 to access the medical records in the medical record storage server 103. The coding system 112 inserts the ICD codes into the medical records 105 and sends an invoice 114 to an appropriate entity such as an insurance company, the government, or a patient. Additionally, the medical records 105 can be examined by a human operator utilizing a core measures system 116, which abstracts data to be reported in a medical quality report 118.

FIG. 1B depicts another embodiment of a medical record storage system and process 150. To facilitate electronic storage, search ability, and subsequent processing, electronic medical record (EMR) system and process 150 forces clinicians to enter medical data into a template 152. The template 152 represents a standard data structure for subsequent processing. Clinicians are generally trained to document medical data in accordance with a "SOAP" note, where "SOAP" stands for subjective, objective, assessment, and plan. The manner in which clinicians are trained during their medical education to document medical records does not easily correlate to a structured template format. Consequently, clinicians may, for example, utilize a comments field in the template 110 to enter medical data, and the template may not be fully populated. Once populated with data from the clinician, the templates are stored as electronic medical records 154. The electronic medical record database 156 attempts to generate invoices 158 and reports 160 based on the electronic medical records 154. The accuracy and completeness of the invoices 158 and reports 160 depends on the accuracy and completeness of the electronic medical records 154. There is no guarantee of the accuracy and completeness of the electronic medical records 154.

Clinicians often utilize paper forms or prepared electronic templates to enter data for recordation in a medical record. A clinician may enter information that is objectively ambiguous or lacks sufficient detail for proper post-processing use. This can be the result of, for example, a clinician's idiosyncrasies, lack of granularity, or colloquialisms in the template. For example, a patient may present with mid-back pain. However, if the clinician records the encounter in a template containing only standardized entries for upper and lower back pain, the clinician may choose the best option available or enter "mid-back pain" in a comments field. The idiosyncrasies manifest in any of a variety of manners. For example, a clinician may enter the term "PT", which may mean a "patient" or mean "physical therapy". The template has no way of interpreting the meaning, and, thus, a human interprets the meaning manually.

After the medical records 105 and 154 are created, government regulations prevent subsequent editing of the medical records 105. Consequently, the medical records 105 and 154 may be inaccurate and, thus, result in inaccurate invoicing and reporting.

SUMMARY OF THE INVENTION

In one embodiment of the present invention, a method includes receiving clinician note data in a first electronic system that includes patient medical-related data. The method further includes processing the clinician note data using a natural language data processor and medical record interpretation rules to automatically convert the clinician note data into an electronic medical record and sending the electronic medical record to a second electronic system to allow review and modification of the electronic medical record. The method further includes receiving feedback data in the first electronic system that indicates modifications to the electronic medical record and processing the feedback data to identify modifications to the electronic medical record. The method also includes analyzing the modifications in the feedback data to determine whether to modify the electronic medical interpretation rules and modifying the medical record interpretation rules in accordance with at least a portion of the feedback data for use in processing subsequently received clinician note data if analysis of the modifications in the feedback data determines to modify the electronic medical interpretation rules.

In another embodiment of the present invention, an apparatus includes one or more processors and a memory, coupled to the one or more processors, and storing code therein that is executable by the one or more processors for:
  receiving clinician note data in a first electronic system that includes patient medical-related data;
  processing the clinician note data using a natural language data processor and medical record interpretation rules to automatically convert the clinician note data into an electronic medical record;
  sending the electronic medical record to a second electronic system to allow review and modification of the electronic medical record;
  receiving feedback data in the first electronic system that indicates modifications to the electronic medical record;
  processing the feedback data to identify modifications to the electronic medical record;
  analyzing the modifications in the feedback data to determine whether to modify the electronic medical interpretation rules; and
  modifying the medical record interpretation rules in accordance with at least a portion of the feedback data for use in processing subsequently received clinician note data if analysis of the modifications in the feedback data determines to modify the electronic medical interpretation rules.

In a further embodiment of the present invention, An tangible, computer readable medium comprising code stored therein and executable by one or more processors for:
  receiving clinician note data in a first electronic system that includes patient medical-related data;
  processing the clinician note data using a natural language data processor and medical record interpretation rules to automatically convert the clinician note data into an electronic medical record;
  sending the electronic medical record to a second electronic system to allow review and modification of the electronic medical record;
  receiving feedback data in the first electronic system that indicates modifications to the electronic medical record;
  processing the feedback data to identify modifications to the electronic medical record;
  analyzing the modifications in the feedback data to determine whether to modify the electronic medical interpretation rules; and
  modifying the medical record interpretation rules in accordance with at least a portion of the feedback data for use in processing subsequently received clinician note data if analysis of the modifications in the feedback data determines to modify the electronic medical interpretation rules.

BRIEF DESCRIPTION OF THE DRAWINGS

The present invention may be better understood, and its numerous objects, features and advantages made apparent to those skilled in the art by referencing the accompanying drawings. The use of the same reference number throughout the several figures designates a like or similar element.

FIG. 8 depicts exemplary eMR elements generated by an automated medical data learning system and an automated eMR learning method.

DETAILED DESCRIPTION

Figure 1A:
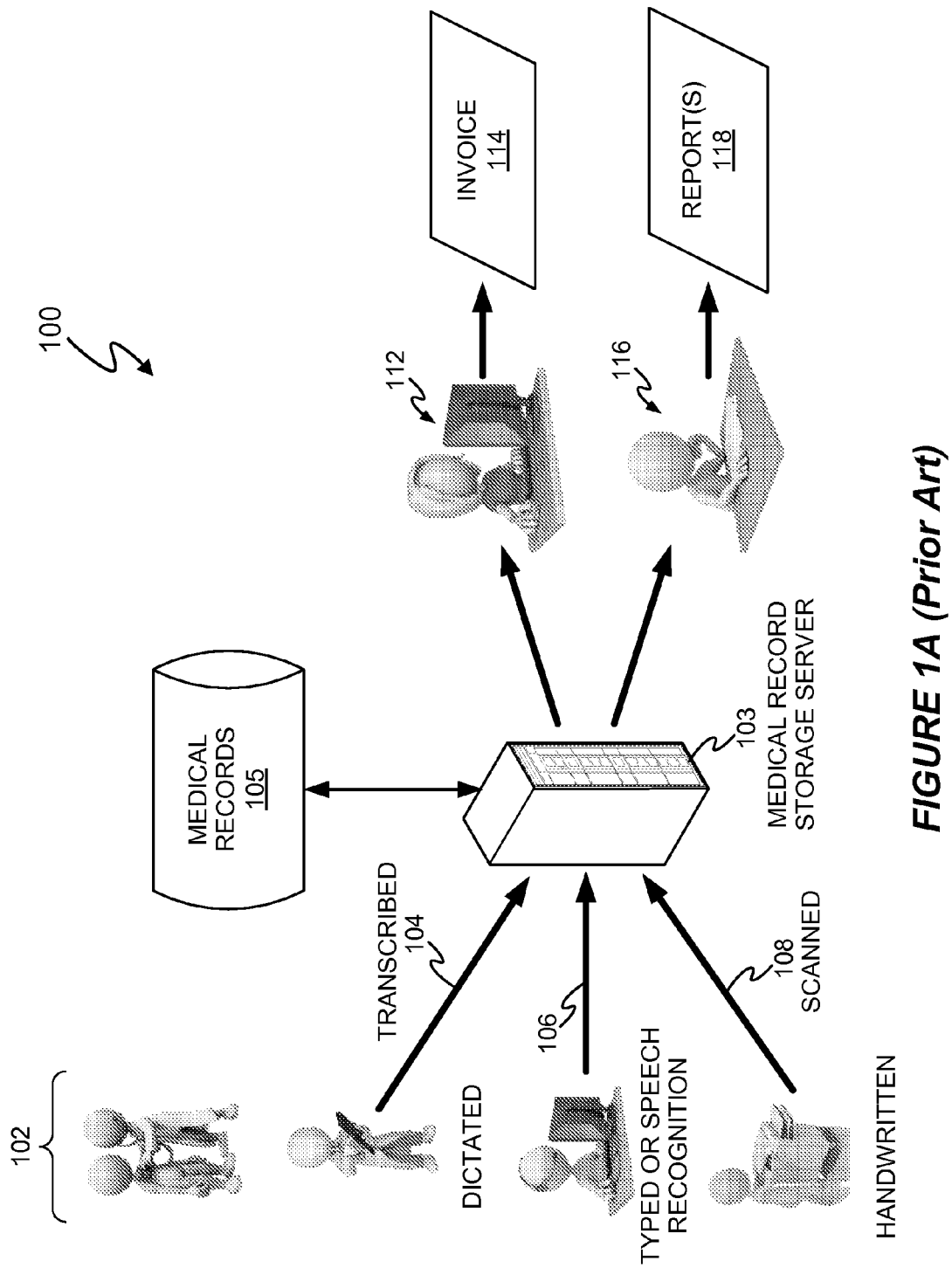
FIGS. 1A and 1B (labeled prior art) depict two embodiments of a medical record storage system and process.
Figure 1B:
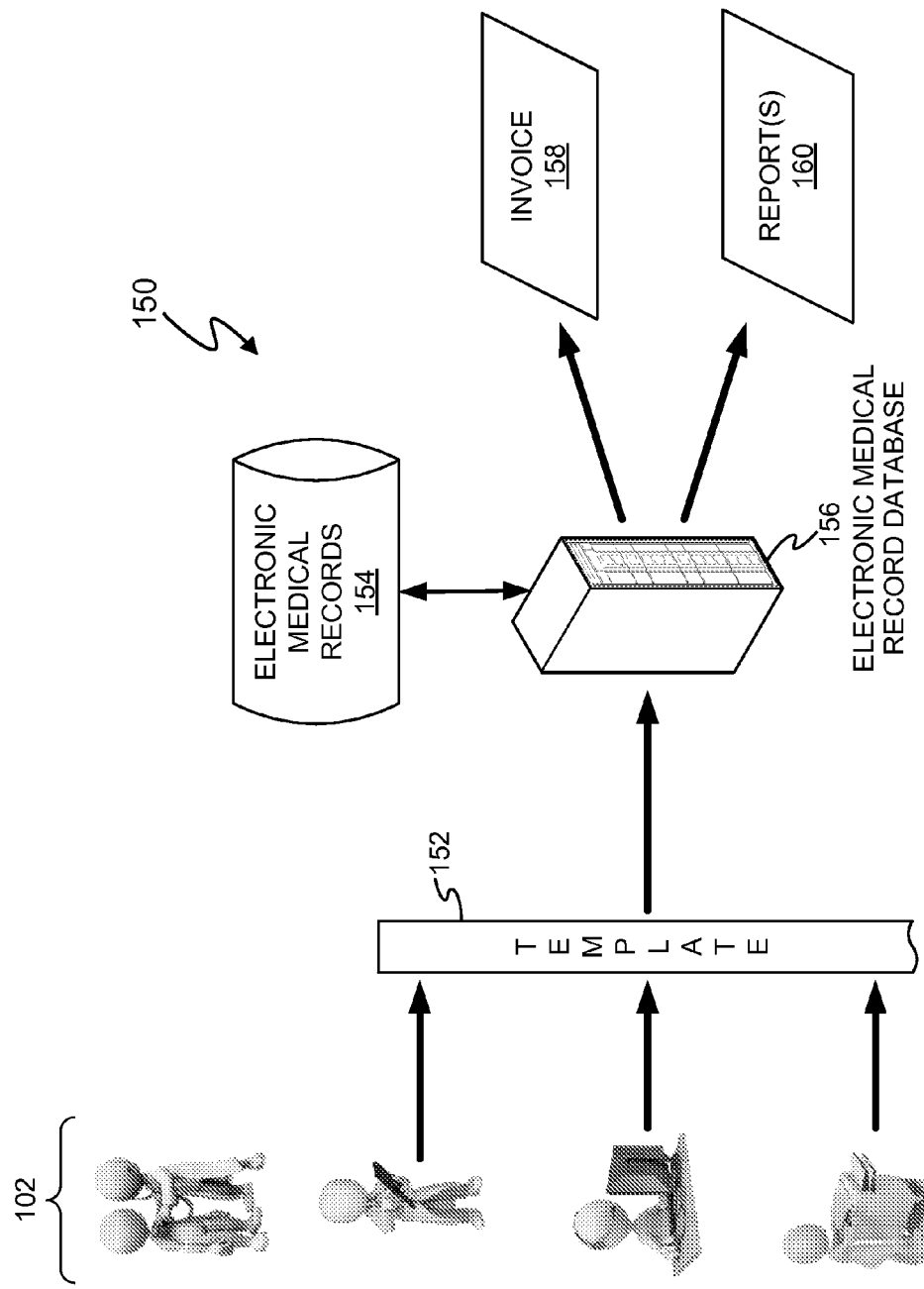

In at least one embodiment, an automated medical data machine learning system and method allow a natural language processing ("NLP") system to automatically learn via, for example, feedback to improve ongoing performance of the natural language processing system. In at least one embodiment, performance can be measured in terms of reducing review time by increasing first pass machine accuracy by the NLP and in terms of automatically identifying areas appropriate for machine learning.

In at least one embodiment, the NLP system provides a paradigm shift in generating a medical record by allowing a clinician increased flexibility in documenting a patient examination and treatment while still generating a structured medical record that facilitates multiple, subsequent processing options. In at least one embodiment, the NLP system utilizes natural language processing and feedback to generate a complete, electronic medical record. Natural language processing allows a clinician to document patient medical-related data without adherence to a specific format or template. The NLP system converts medical-related data into electronic text input data, and a natural language processor generates a medical record in accordance with a template. Thus, the NLP system allows the clinician to document patient information including examination and treatment information in a manner in which the clinician is trained, while still storing a reflective medical record in accordance with a template. In at least one embodiment, the NLP system recognizes particular data in medical-related electronic text and processes the text as, for example, described in U.S. patent application Ser. No. 13/599,601, filed Aug. 30, 2012, entitled "Medical Record Generation and Processing", and inventors Kenneth R. Chatfield and Christopher B. Smith (referred to herein as the "NLP Patent"). The NLP Patent is hereby incorporated by reference in its entirety.

In at least one embodiment, the NLP system utilizes a medical ontology to facilitate knowledge processing by the natural language processor. In at least one embodiment, the medical ontology provides semantic information and contextual interrelationships between various semantic concepts. In at least one embodiment, the medical ontology allows the natural language processor to perform contextual analysis of data to determine the accuracy and completeness of the draft medical record. The medical ontology facilitates intelligent, context-based indexing, searching, selection, retrieval, data mining, and analysis of the draft and complete, final medical records.

However, in at least one embodiment, the NLP system is not 100% accurate. For example, the natural language processing may misinterpret some portion of input data or be unable to resolve certain ambiguities in the input data. Often misinterpretations and ambiguities arise from data that has multiple meanings or has no predefined meaning. In at least one embodiment, the automated medical data learning system and method receives responsive, corrective and positive affirmation feedback provided by a clinician for a draft medical record generated by the NLP system. In at least one embodiment, the automated medical data learning system and method processes the responsive feedback and learns from the correction, positive affirmation, and various other factors associated with the corrections. Exemplary other factors include the particular clinician associated with the feedback in order to learn idiosyncrasies or colloquialisms of this particular clinician, the medical specialty of the clinician, the location of the clinician, and other factors that inform the learning process. Based on the feedback, the automated medical data learning system and method can improve the interpretation by the NLP system of future input data. Furthermore, the automated medical data learning system and method can learn from other feedback sources such as a medical coding system and a medical core measures system that respectively provide medical coding feedback data and medical core measures feedback data.

The particular technology for improving the interpretation by the NLP system of future input data is a matter of design choice. For example, in at least one embodiment, the automated medical data learning system and method includes a linguistics module that determines the part of speech of a particular term or term, such as use as a noun or verb. In at least one embodiment, the automated medical data learning system and method learns an interpretation based on a source of the input data such as from a particular medical specialty, a particular clinician, a particular medical facility location, or any other data that may be indicative of a particular interpretation. In at least one embodiment, the automated medical data learning system and method includes a statistics module that allows the automated medical data learning system and method to determine a most probable interpretation or multiple interpretations. In at least one embodiment, the interpretations are ordered by a likelihood of correctness.

In at least one embodiment, learning by the automated medical data learning system and method is an ongoing process. As the automated medical data learning system and method receives more feedback, the automated medical data learning system and method can continue to improve the accuracy of the initial NLP system output data. The learning results are, for example, expressed in a set of rules used by the NLP system to process input data. The automated medical data learning system and method updates the rules to, for example, continually improve performance of the NLP system.

Figure 2:
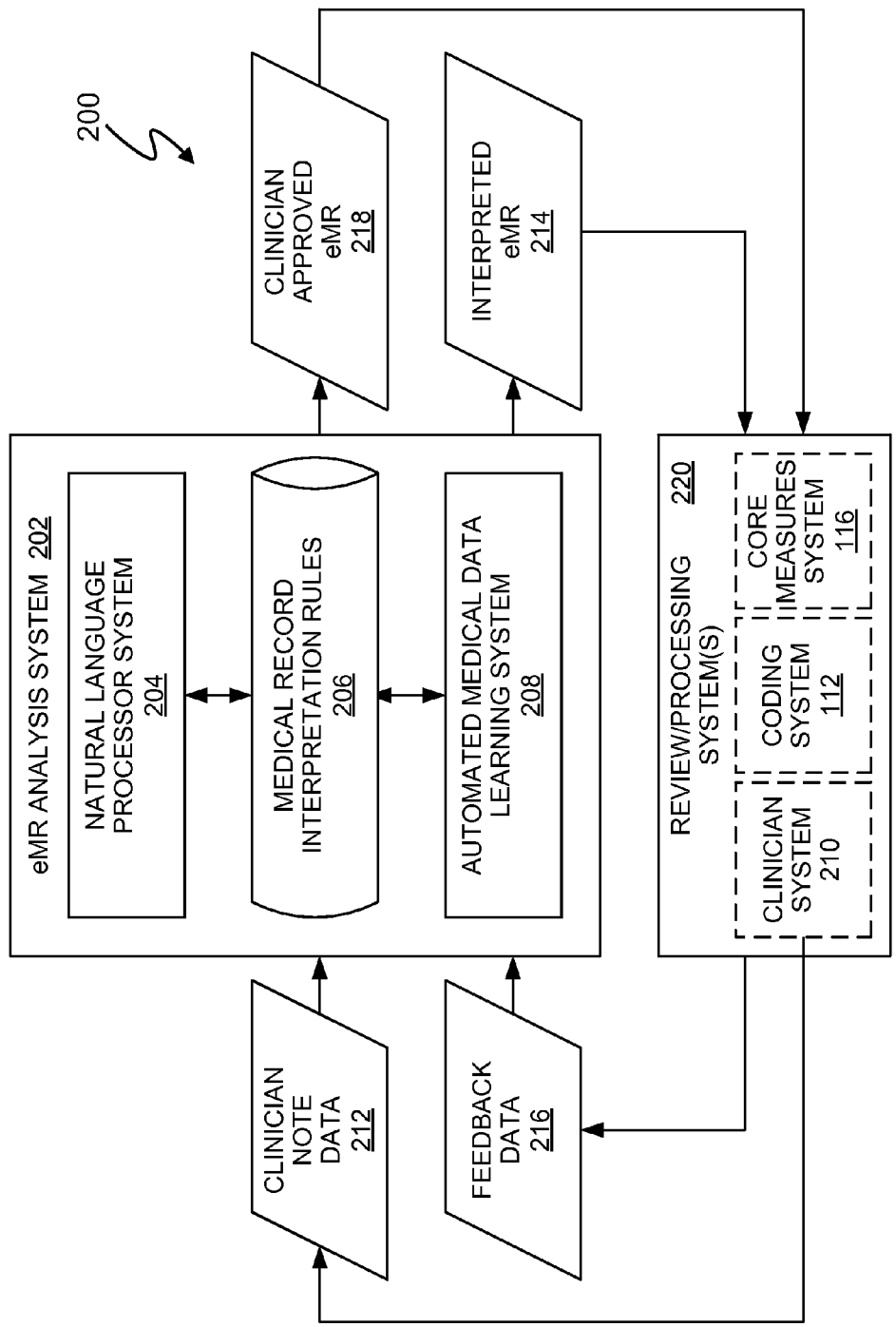
FIG. 2 depicts a medical data processing system that includes an automated electronic medical record (eMR) analysis and learning system.

FIG. 2 depicts a medical data processing system 200 that includes an automated machine electronic medical record (eMR) analysis and learning system 202, which in at least one embodiment includes an automated medical data learning system 208. In at least one embodiment, the eMR analysis and learning system 202 represents a machine learning system that automatically learns from modifications made in an electronic version of a medical record and updates a rule set so that a NLP system improves automated processing accuracy over time. The automated eMR analysis and learning system 202 receives at least two sets of input data, namely clinician note data 212 and feedback data 216. In at least one embodiment, the clinician note data 212 represents output data from a natural language process (not shown), such as the natural 212 process described in the NLP Patent. In at least one embodiment, the clinician note data 212 originates from a record of a particular medical encounter, such as a physician's note made during or after a physician interview and examination. In at least one embodiment, as described in the NLP Patent, a NLP system processes clinician input data and determines particular aspects of the clinician input data, such as the context of the data and meaning of particular terms, such as does "PT" mean "patient" or "physical therapy." The NLP system then generates the clinician note data 212. In at least one embodiment, the clinician note data 212 is generated in the form of machine-readable ASCII text.

In at least one embodiment, the clinician note data 212 is provided in an electronic form to the eMR analysis and learning system 202, which uses the natural language processor (NLP) system 204 to process the clinician note data 212 and generate an interpreted eMR 214. In at least one embodiment, the interpreted eMR 214 is generated according to medical record interpretation rules 206, which are used by the NLP system 204 when generating the interpreted eMR 214. In at least one embodiment, the eMR 214 highlights data to request particular feedback, presents questions for particular feedback, and provides text for which the NLP system 204 had not interpretation issues. The resulting interpreted eMR 214 is then processed by one or more review and processing system(s) 220 to generate feedback data 216. In at least one embodiment, the automated medical data learning system 208 compares the feedback data with the original eMR 214 to determine the changes between the eMR 214 and the feedback data 216. The changes allow the automated medical data learning system 208 to record comparison results and responsive answers to questions and either store the results and answers in a memory (not shown) for future processing or update the medical record interpretation rules 206. When the automated medical data learning system 208 stores the results, the results can, for example, provide statistical data for future updates to the rules 206. For example, in at least one embodiment, the automated medical data learning system 208 updates the rules when the same responsive feedback is obtained X % of the time by a particular clinician, clinicians having a particular specialty, clinicians from a particular medical facility, and any other factors that can inform consistently correct interpretation of the clinician note data 212. The value of X is a matter of design choice, such as more than 50.

In at least one embodiment, the feedback data 216 includes one or more of coding feedback data, core measures feedback data, or clinician feedback data. The feedback data 216 reflects an outcome of a review of the interpreted eMR 214 by one or more of the review and processing system(s) 220 and provides one of the mechanisms for improving interpretation of the clinician note data 212. The particular composition of the review and processing system(s) 220 are a matter of a design choice.

In at least one embodiment, the review and processing system(s) 220 include a clinician system 210 operated by the clinician who originally generated the clinician note data 212 that was processed to generate the interpreted eMR 214. In at least one embodiment, the clinician uses the clinician system 210 to review the interpreted eMR 214 and generate clinician feedback data 216, which in turn is processed with the clinician note data 210. The review process involves only one feedback pass. In at least one embodiment, the review and processing system(s) 220 generate one or more iterations of the interpreted eMR 214. In at least one embodiment, the interpreted eMR 214 is provided to the clinician system 210 for clinician review until it is approved by the clinician, at which time the interpreted eMR 214 is processed to generate a clinician approved eMR 218.

The automated medical data learning system 208 updates the medical record interpretation rules 206 based on the automated review of the feedback data 216, which improves the operation of the NLP system 204. In at least one embodiment, the automated medical data learning system 208 improves performance of the NLP system 204 by improving correlation between the interpreted eMR 214 and one or more review and processing system(s) 220 that review the interpreted eMR 214. In at least one embodiment, the review and processing system(s) 214 include a coding data processing system 112 that reviews the clinician approved eMR 218 for accurate charge codes, and/or a core measures data processing system 116 that reviews the clinician approved eMR 218 for compliance with medical care guidelines and regulations.

Figure 3:
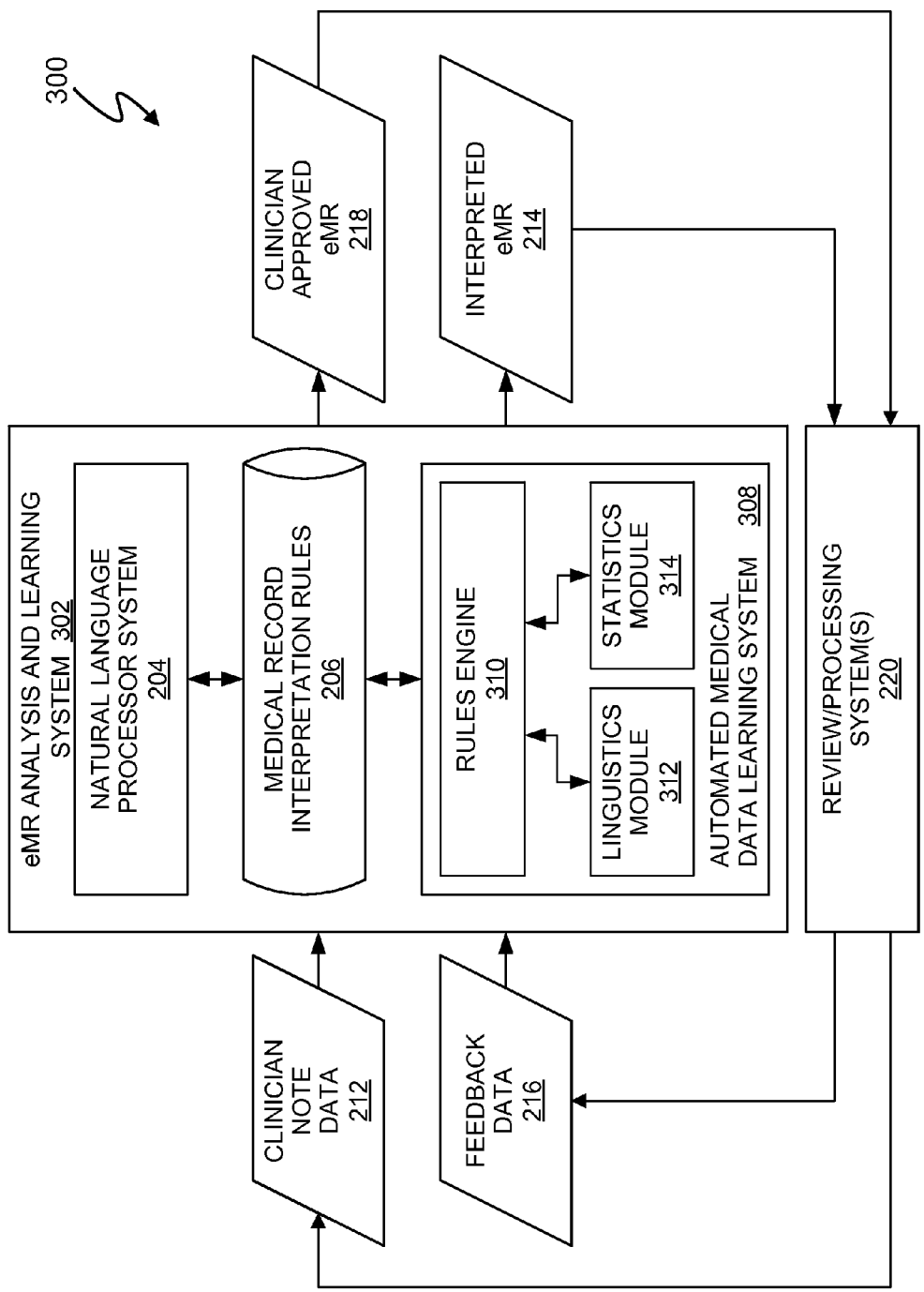
FIG. 3 depicts an embodiment of the automated eMR analysis system of FIG. 2.

FIG. 3 depicts a medical data processing system 300 that includes an automated electronic medical record (eMR) analysis system 302. The eMR analysis system 302 represents one embodiment of the eMR analysis and learning system 202 depicted in FIG. 2. The eMR analysis system 302 includes an automated medical data learning system 308, which represents one embodiment of the automated medical data learning system 208 depicted in FIG. 2. The medical data processing system 300 is otherwise identical to the medical data processing system 200 depicted in FIG. 2.

In at least one embodiment, the automated medical data learning system 308 includes a rules engine 304, which is used to manage the medical record interpretation rules 206 that are used by the natural language processor (NLP) system 204 to process the clinician note data 210 to generate the interpreted eMR 212. In at least one embodiment, the rules engine 304 identifies terms of interest, such as abbreviations and medical or colloquial terms. In at least one embodiment, feedback data 216 is used by the rules engine 304 to update the medical record interpretation rules 206.

In at least one embodiment, the automated medical data learning system 302 includes a linguistics module 312. In at least one embodiment, the linguistics module 312 analyzes the linguistics of the clinician note data 212 and terms of interest, such as sentence structure, what part of speech is a term of interest (e.g., noun, verb, adjective, adverb), the number of occurrences of the term, origin of the clinicians note data (e.g., a particular clinician, practice area, regional area, experience level, etc.), and any other analysis that assists in accurately interpreting the term of interest. An exemplary linguistics module framework is available from International Business Machine Corp. of Armonk, N.Y. In at least one embodiment, the linguistics module 312 is used by the rules engine 310 to process the clinician note data 210 to manage the medical record interpretation rules 206.

In at least one embodiment the automated medical data learning system 302 includes a statistics module 314. In at least one embodiment, the statistics module 314 performs a statistical analysis of the terms of interest to assign a probability to possible interpretations of the term of interest based on the linguistics analysis. For example, if the clinician note is from an ear, nose throat (ENT) doctor and the diagnosis is not "speech related" then there is a 90% chance that the abbreviation "PT" stands for patient. If the "present illness" in the clinician note data 212 is a 'shoulder injury' and "PT" is used as a direct object, then "PT" stands for physical therapy. In at least one embodiment, the statistics module 314 is used by the rules engine 310 to process the clinician note data 210 to manage the medical record interpretation rules 206.

In at least one embodiment the automated medical data learning system 302 includes both a linguistics module 312 and a statistics module 314. In at least one embodiment, both the linguistics module 312 and the statistics module 314 are used by the rules engine 304 to process the clinician note data 210 to manage the record interpretation rules 206.

Figure 4:
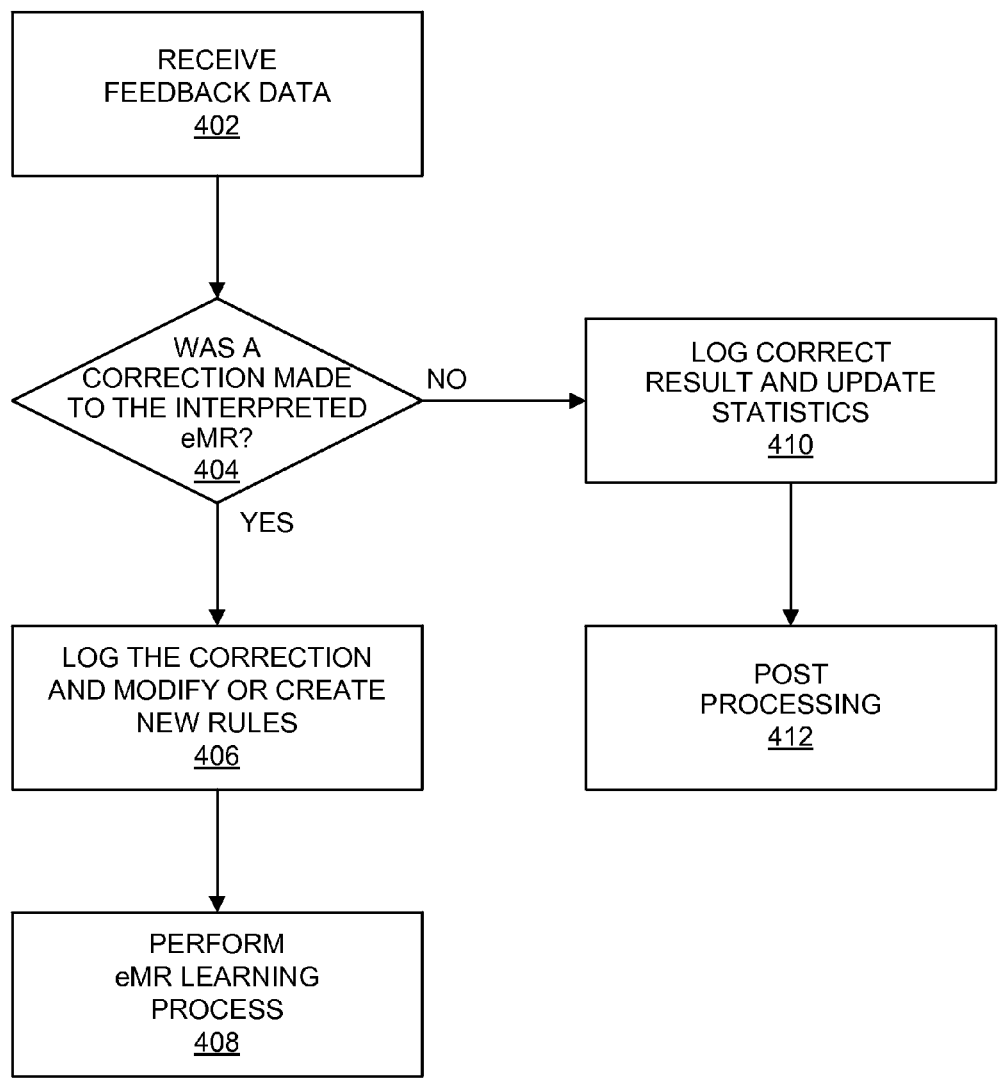
FIG. 4 depicts an embodiment of an automated eMR learning process for the system of FIGS. 2 and 3.

FIG. 4 depicts an embodiment of an automated electronic medical record (eMR) learning process (eMR LP) for the system of FIGS. 2 and 3. Referring to FIGS. 2 and 3, feedback data 216 is respectively received in operation 402 by the eMR analysis and learning system 202 or 302. The feedback data 216 can originate from one or more sources, such as the clinician system 210, the coding system 112, or the core measures system 116. The feedback data 216 provides at least two general categories of information that are useful in the learning process: (1) corrections to the original natural language processing (NLP) output data, and (2) an absence of corrections. Both are used by the automated medical data learning system 202 or 302 in operation 404 to determine whether a correction was made to the interpreted eMR 214 by one or more of the review/processing system(s) 220.

If it was determined in operation 404 that a correction was made, then the first category is used in Operation 406 to log the correction and to modify or create new medical record interpretation rules 206. The updated medical record interpretation rules are then used in operation 408 by the automated medical data learning system 208 or 308 to perform eMR learning processes. However, if it was determined in operation 404 that no correction was made, then the correct interpretive result is logged and the eMR learning statistics are updated by the statistics module 314 in operation 410, followed by post processing of the clinician approved eMR 218 in operation 412.

However, in at least one embodiment, the correction may not be used to modify or create a new rule in operation 406. If the statistics module 314 indicates that the interpretive error was actually a correct interpretation X % of the time, then the eMR LP will log a decrease in the percentage of reliability of the interpretation but may not nullify the medical record interpretation rule 206 that caused the erroneous interpretation. In another embodiment, an error can nullify a rule that caused the erroneous interpretation. The speed at which the eMR LP updates the medical record interpretation rules 206 is a matter of design choice. For example, "FX" may be quickly learned to mean "family history" and a rule is written for this interpretation. However, some terms may occur infrequently and won't be written as a rule until a particular statistical confidence interval is reached.

The medical record interpretation rules 206 themselves are operations that analyze the NLP input data. Exemplary rules process the NLP input data in accordance with the following analytics: (1) word count, (2) parts of speech, (3) medical ontologies, (4) metadata (e.g., identification of the clinician, hospital or clinic, region, specialty, etc.). The medical record interpretation rules can be of any form, such as "if, then, else" rules. For example, if a clinician's medical specialty is orthopedics, then PT=physical therapy, else PT=patient.

Figure 5:
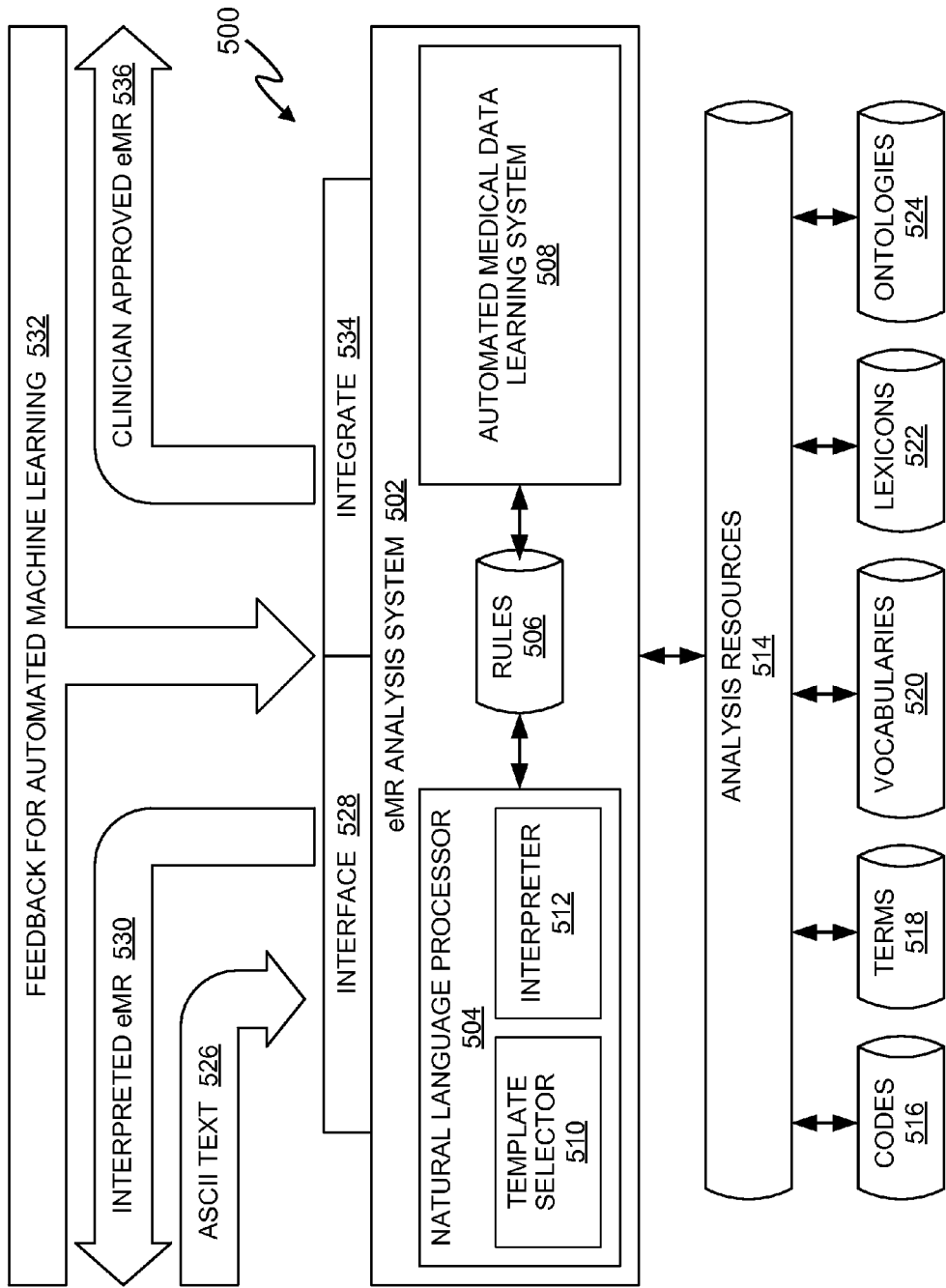
FIG. 5 depicts a natural language processing and feedback enabled medical record generation and processing system that includes an eMR analysis system.

FIG. 5 depicts a natural language processing and feedback enabled medical record generation and processing system 500 that includes an electronic medical record (eMR) analysis system 502. In at least one embodiment, the eMR analysis system 502 includes an automated medical data learning system 508. In at least one embodiment, the medical record generation and processing system 500 is uses natural language processing, machine learning, various data sources, and feedback from one or more review and processing systems to generate a complete and accurate electronic medical record (eMR).

In at least one embodiment, clinician note data in the form of ASCII text 526 is received by the eMR analysis system 502 through interface module 528. The eMR analysis system 502 then processes the ASCII text 526 to generate an interpreted eMR 530. In at least one embodiment, the eMR analysis system 502 includes a natural language processor (NLP) system 504 and an automated medical data learning system 508. In at least one embodiment, the NLP system 504 includes a medical record template selector module 510 and an interpreter module 512. In at least one embodiment, the eMR analysis system 502 uses analysis resources 514 when generating the interpreted eMR 530. In at least one embodiment, the analysis resources 514 include one or more of codes 516, terms 518, vocabularies 520, lexicons 522, or ontologies 524.

In at least one embodiment, the NLP system 504 uses the template selector 510 to select a target medical record template, which is then populated by the NLP system 504 to generate the interpreted eMR 530. In at least one embodiment, the NLP system 504 uses the interpreter module 512 to process the ASCII text 526 when populating the target medical record template. In at least one embodiment, the NLP system 504 may generate annotations when it is populating the target medical record template. As an example, the ASCII text 526 contained in a clinicians note may include the term "PT," which could be interpreted as an abbreviation for "patient" or as an acronym for "physical therapy." In at least one embodiment, these annotations are appended to the interpreted eMR 530 by the NLP system 504 and then provided through interface 528 for clinician review and feedback 532. Feedback for automated medical data learning 532 is then received, which in turn is processed by the eMR analysis system 502 to generate a clinician approved eMR 536. In at least one embodiment, the clinician approved eMR 536 is provided through the interface module 536 for post processing by other systems.

In at least one embodiment, the automated medical data learning module 508 keeps track of feedback data resulting in corrections to the interpreted eMR 530. This feedback data, and the resulting corrections to the interpreted eMR 530, are processed by the automated medical data learning module 508 to generate additional and relevant questions, which are then presented to the clinician to facilitate the provision of their feedback 532. In at least one embodiment, the automated medical data learning module 508 analyzes statistical history to generate additional and relevant questions. In at least one embodiment, the statistical analysis includes the automated medical data learning module 508 identifying variables that affect one or more of the medical record interpretation rules 506. In at least one embodiment, the processing of the feedback 532 by the eMR analysis system 502 results in the selection of a different (e.g., more medically appropriate) medical record template by the template selector 510. In this embodiment, the data from the previously-populated medical record template is transferred by the NLP system 504 to the newly selected medical record template, which is then processed to generate the interpreted eMR 530 used for subsequent processing.

In at least one embodiment, feedback from more experienced or more capable clinicians is used by the automated medical data learning module 508 to generate the additional and relevant questions. In at least one embodiment, a predetermined group of clinicians consistently provide the same corrective feedback for a NLP interpretation of a clinician note. As a result, the NLP interpretation is revised to improve accuracy and to reduce the amount of feedback received from the predetermined group of clinicians in the future. In at least one embodiment, the revision includes modifying the medical record interpretation rules 506 so that processing of subsequent clinician note data has a higher probability of accuracy and completeness.

In at least one embodiment, the automated medical data learning module 508 is trained by modifying or creating new medical record interpretation rules 506. In at least one embodiment, the medical record interpretation rules 506 are modified or created in accordance with a predetermined group of clinicians associated with a geographic locale. As an example, Lyme disease is more common in the Northern part of the U.S. than it is in the South. As a result, the NLP interpretation of a clinician note that originated from a clinic in Vermont would be more oriented to Lyme disease than West Nile virus, which is more common in sub-tropical areas. In at least one embodiment, the medical record interpretation rules 506 are modified or created in accordance with one or more clinicians associated with a medical specialty or a medical facility. As an example, a pediatrician may use the abbreviation "PT" to refer to a patient, while an orthopedist would use the same abbreviation to refer to physical therapy. To further the example, a clinician at a children's hospital may likewise use the abbreviation "PT" to refer to a patient, while a clinician at a physical rehabilitation facility may likewise us the same abbreviation to refer to physical therapy. As a result, if "PT" is used by a private practice pediatrician or a clinician at a children's hospital, then the medical record interpretation rules 506 would include a rule stating that PT=patient. Conversely, if "PT" is used by a private practice orthopedist or a clinician at a physical therapy rehabilitation facility, then the medical record interpretation rules 506 would include a rule stating that PT=physical therapy.

In at least one embodiment, the medical record interpretation rules 506 are modified or created in accordance with the context of a clinician's medical specialty. In this embodiment, the clinician's medical specialty provides the context for the NLP interpretations as well as the basis for training the automated medical data learning module 508. In at least one embodiment, the medical record interpretation rules 506 are modified or create in accordance with feedback that is consistently the same for a predetermined clinician or patient. In this embodiment, the consistent feedback provides the context for the NLP interpretation as well as the basis for training the automated medical data learning module 508. In at least one embodiment, the medical record interpretation rules 506 are customized in accordance with a patient's demographics. Once feedback for automated machine learning 532 is received from a clinician signifying that the interpreted eMR 530 is correct, it is provided as a clinician approved eMR 536 through an integration module 534 for further processing.

Figure 6:
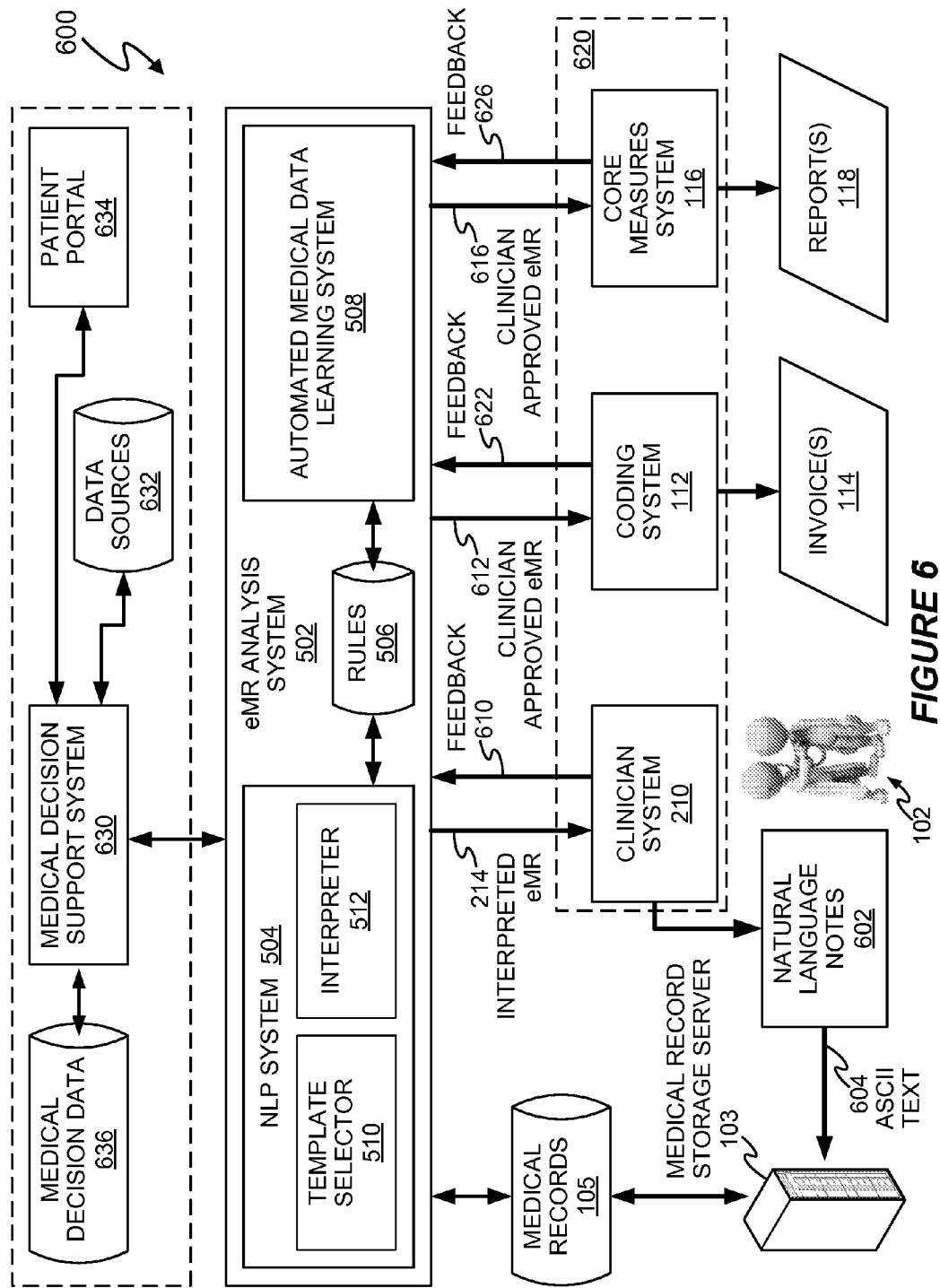
FIG. 6 depicts an embodiment of the system of FIG. 5.
Figure 7:
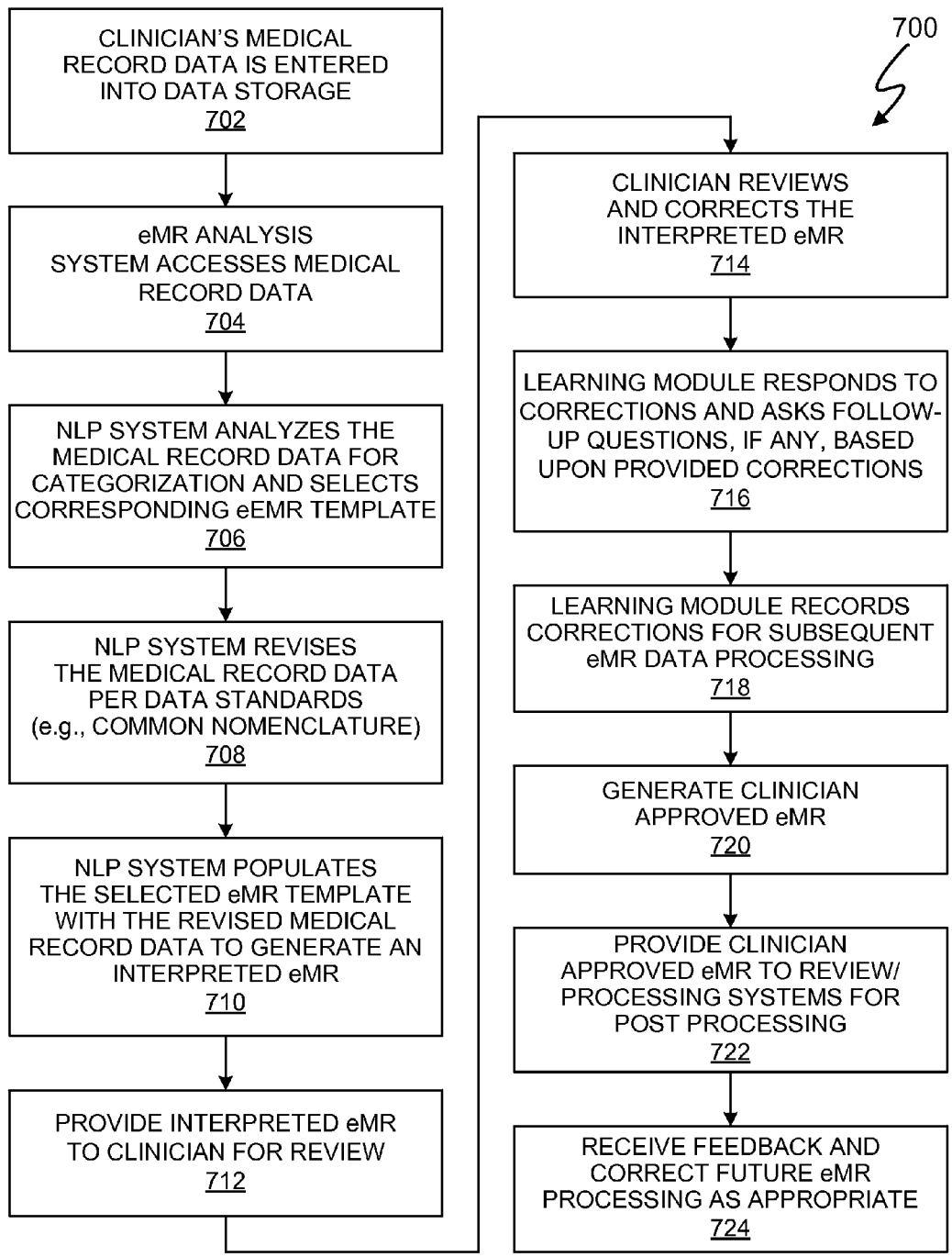
FIG. 7 depicts an exemplary natural language processing and automated eMR learning process for the system of FIGS. 5 and 6.

FIG. 6 depicts an embodiment of the system of FIG. 5. In at least one embodiment, the medical record generation and processing system 600 generates an interpreted eMR 214. In at least one embodiment, the medical record generation and processing system 600 generates a clinician approved eMR 612 or 616. In at least one embodiment, the automated eMR learning system 600 operates in accordance with an automated eMR learning method 700. FIG. 7 depicts the automated eMR learning process 700.

Referring to FIGS. 5 and 6, operation 702 enters the clinician's 102 medical record data into data storage in the form of medical records 105. The manner of entering the medical record data is a matter of design choice. In at least one embodiment, the medical record data is obtained from any of a variety of sources, such as a patient, administrators, and clinicians. In at least one embodiment, the medical record data is collected from the variety of sources in the form of natural language notes 602. In at least one embodiment, the natural language notes 602 are provided in the form of ASCII text 604 to the medical record storage server 103.

Operation 704 accesses the medical data record for processing by the natural language processor (NLP) system 504 of the eMR analysis system 502. In operation 706, the NLP system 504 analyzes the medical record data for categorization and selects a corresponding eMR template. In at least one embodiment, the corresponding eMR template is selected by the template selector module 510. The medical record data is then revised in operation 708 by the NLP system 504 per predetermined data standards, such as a common nomenclature. In at least one embodiment, the revisions are performed by the interpreter module 512. Then, in operation 710, the selected eMR template is populated by the NLP system 504 with the revised medical data.

In operation 712, the eMR analysis system 502 provides the populated eMR template in the form of an interpreted eMR 214 to a clinician system 210, which is used by the clinician 102 to review the eMR 214. In operation 714, the clinician 102 reviews and corrects the interpreted eMR 214 in the form of feedback 610. In at least one embodiment, the provision of the feedback 610 in operation 714 is virtually real-time and allows personnel to utilize any electronic device, such as a tablet personal computer, a laptop personal computer, an intelligent phone, or any other electronic data processing system, to review the interpreted eMR 214 for accuracy and completeness.

The automated medical data learning module 502 then responds to the corrections contained in the clinician's feedback 510 in operation 716. As an example, the automated medical data learning module 502 may make corrections to the interpreted eMR 214 and ask follow-up questions, if any, based upon the provided corrections. As another example, if the corrections raise a new issue, such as core quality, then the automated medical data learning module 502 prompts the clinician 102 for additional feedback 610. In operation 718, the NLP system 504 logs corrections for subsequent eMR data processing. In at least one embodiment, the corrections are used by the automated medical data learning system 508 to update the medical record interpretation rules 506. Operations 712 through 718 are then repeated until the clinician 102 signifies that the interpreted eMR 214 is sufficiently corrected and completed to generate a clinician approved eMR 612 or 616, which is generated in operation 720.

Then, in operation 722, the clinician approved eMR 612 or 616 is forwarded to one or more review and processing system(s) 620. In at least one embodiment, the one or more review and processing system(s) includes a coding system 112 and/or a core metrics system 116, which respectively generate invoice(s) 114 and core measures report(s) 118. In at least one embodiment, the generation of invoice(s) 114 includes review of billing codes and other audit operations. In at least one embodiment, the generation of report(s) 118 includes the performance of core measures operations. In operation 724, feedback 612 and 616 is respectively received from the coding system 112 and core measures system 116 by the eMR analysis system 502 and future eMR processing is corrected as appropriate.

In at least one embodiment, the medical record generation and processing system 600 also includes a medical decision support system 630. In at least one embodiment, the medical decision support system 630 receives data from multiple sources including from the NLP system 504, data sources 623, such as medical treatment and pharmaceutical sources, and from patients via a patient portal 634. Data from the NLP system 504 allows the medical decision support system 630 to ascertain the current medical condition of the patient and any treatment options recommended by the clinician 102. In at least one embodiment, the medical decision support system 630 processes the medical condition and any treatment options in accordance with expert data from the data sources 632 to provide diagnosis and treatment options for storage as medical decision data 636. The patient portal 634 allows patients to provide feedback regarding one or more past visits with a clinician 102. The feedback allows the patient, for example, to provide data on the effectiveness of various treatments including the effectiveness of medications. The patient portal 634 can utilize any data communication technology, such as a web browser based user interface displayed on a client computer and content provided by the medical decision support system 630. Thus, in at least one embodiment, the patient portal 634 allows the medical record generation and processing system 600 to collect outcomes of treatment. Collecting outcomes can have special significance when a patient does not return to the treating clinician 102, but the patient's feedback is available to subsequent treating clinicians 102. Additionally, patient feedback can provide empirical data regarding the effectiveness of treatments and other perceptions of the patient related to the examination and treatment process.

In at least one embodiment, the medical decision support system 630 utilizes patient supplied information obtained via the patient portal 634 to customize the diagnosis and treatment of the patient. For example, if the patient responds well to certain medications or has a history of certain medical conditions, the medical support system 630 can take this information into account when making recommendations. Additionally, in at least one embodiment, the medical decision support system 630 performs a statistical analysis on the data received by the medical decision support system 630 to determine or obtain a measure of effectiveness of treatment options in terms of, for example, a percentage of effectiveness relative to a particular population. For example, if a patient 'A' presents with condition 'B', the 'X' percent of the population respond well to medication 'Y', 'R' percent of the population will respond well to medication 'Z', and so on. The particular population is a matter of design choice. For example, the population may be selected from a specific age group, a specific geographic area, or a specific gender to provide the most relevant data. In at least one embodiment, if the clinician 102 overrides the recommended diagnosis and treatment, the clinician 102 is prompted to provide further data in the medical record 105 to justify the override.

FIG. 8 depicts exemplary electronic medical record (eMR) elements 800 generated by the automated medical data learning system 600 and the automated eMR learning method 700. Referring to FIG. 8, the eMR elements 800 includes a plurality of automated eMR machine learning elements 802 and a plurality of resulting eMR template entries 812 used to automatically populate an eMR. In at least one embodiment, the eMR machine learning elements include "dictated text from clinician" 804, "automated decision" 806, "clinician feedback" 808, and "final decision" 810.

As an example, dictated text received from a clinician 804 may state that the diagnosis for a patient is chronic renal insufficiency. The dictated text is processed as described in operations 706, 708, and 710 of the automated eMR machine learning method 700 to generate automated decision 806, which is used to populate a selected eMR template with "diagnosis: chronic kidney disease (CKD)." As described in operation 712 and 714 of the automated eMR machine learning method 700, the automated decision 806 is provided to the clinician for feedback 808, who responds positively to the substitution of "chronic kidney disease (CKD)" in place of "chronic renal insufficiency." As a result, the eMR template is populated with the final decision 810 of with "diagnosis: chronic kidney disease (CKD)."

As another example, dictated text received from a clinician 804 may state that the patient admits to using 8 to 10 packets a day of snus, which is a form of tobacco. The dictated text is processed as described in operations 706, 708, and 710 of the automated eMR machine learning method 700 to generate automated decision 806, which is used to populate a selected eMR template with "tobacco use: negative." As described in operation 712 and 714 of the automated eMR machine learning method 700, the automated decision 806 is provided to the clinician for feedback 808, who responds negatively to the substitution of "tobacco use: negative" and provides feedback that "snus is a positive indicator for tobacco use." As a result, the eMR template is populated with the final decision 810 of with "tobacco use: positive."

As yet another example, dictated text received from a clinician 804 may state that the patient presents underweight, with an albumin level of 3.0. The dictated text is processed as described in operations 706, 708, and 710 of the automated eMR machine learning method 700 to generate automated decision 806, which is used to populate a selected eMR template with "history of present illness: malnutrition." As described in operation 712 and 714 of the automated eMR machine learning method 700, the automated decision 806 is provided to the clinician for feedback 808, who responds with "negative feedback for albumin level of 3.0 indicating severe malnutrition." As a result, the eMR template is populated with the final decision 810 of with "history of present illness: moderate malnutrition."

Figure 9:
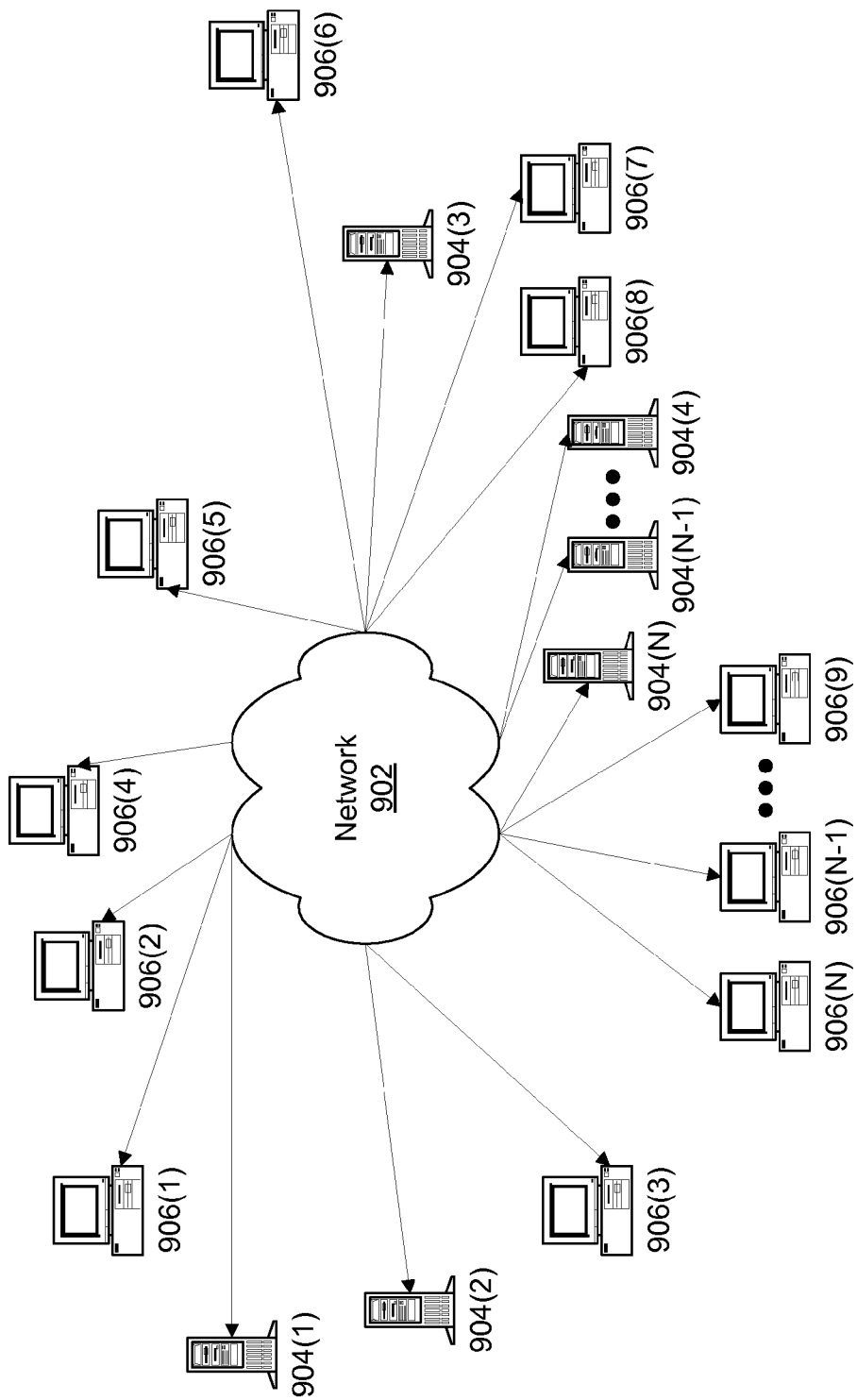
FIG. 9 depicts a block diagram illustrating a network environment in which the systems of FIGS. 5 and 6 and the process of FIG. 7 can be performed.

FIG. 9 depicts a block diagram illustrating a network environment in which the medical record generation and processing system 500 and 600 and the automated electronic medical record (eMR) learning method 700 may be performed. Network 902 (e.g. a private wide area network (WAN) or the Internet) includes a number of networked server computer systems 904(1)-(N) that are accessible by client computer systems 906(1)-(N), where N is the number of server computer systems connected to the network. Communication between client computer systems 906(1)-(N) and server computer systems 904(1)-(N) typically occurs over a network, such as a public switched telephone network over asynchronous digital subscriber line (ADSL) telephone lines or high-bandwidth trunks, for example communications channels providing T1 or OC3 service. Client computer systems 1006 (1)-(N) typically access server computer systems 904(1)-(N) through a service provider, such as an internet service provider ("ISP") by executing application specific software, commonly referred to as a browser, on one of client computer systems 906(1)-(N).

Client computer systems 906(1)-(N) and/or server computer systems 904(1)-(N) may be, for example, computer systems of any appropriate design, including a mainframe, a mini-computer, a personal computer system including notebook computers, a wireless, mobile computing device (including personal digital assistants). These computer systems are typically information handling systems, which are designed to provide computing power to one or more users, either locally or remotely. Such a computer system may also include one or a plurality of input/output ("I/O") devices coupled to the system processor to perform specialized functions. Mass storage devices such as hard disks, compact disk ("CD") drives, digital versatile disk ("DVD") drives, and magneto-optical drives may also be provided, either as an integrated or peripheral device represent examples of tangible, computer readable media. One such example computer system is shown in detail in FIG. 10.

Figure 10:
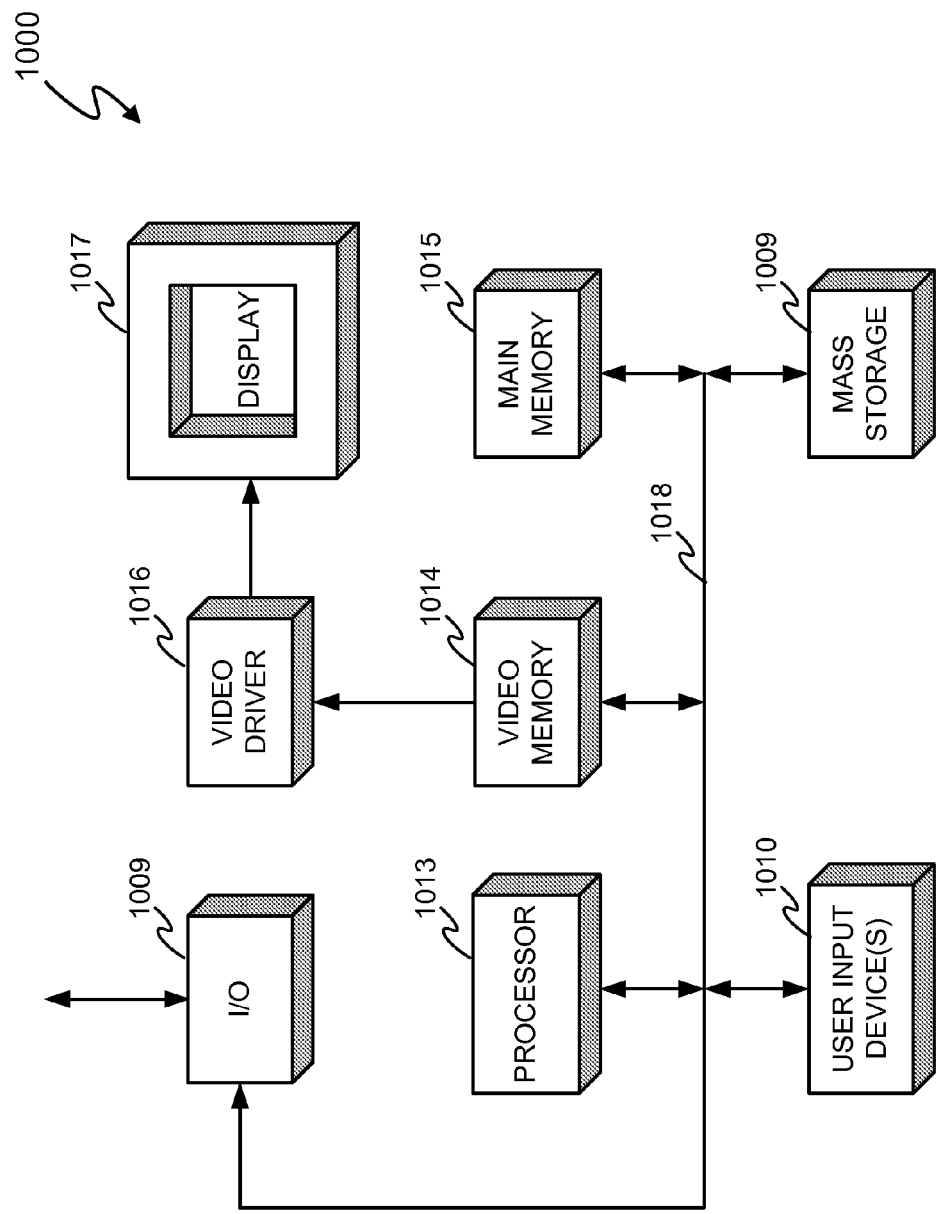
FIG. 10 depicts an exemplary computer system.

Embodiments of the medical record generation and processing system 500 and 600 and the automated electronic medical record (eMR) learning method 700 can be implemented in any medium, such as in the computer system 1000 of FIG. 10 operating in accordance with a computer program or in specifically designed hardware, such as hardware implemented using field programmable gate arrays.

Input user device(s) 1010, such as a keyboard and/or mouse, are coupled to a bi-directional system bus 1118. The input user device(s) 1010 are for introducing user input to the computer system and communicating that user input to processor 1013. The computer system of FIG. 10 generally also includes a video memory 1014, main memory 1015 and mass storage 1009, all coupled to bi-directional system bus 1018 along with input user device(s) 1010 and processor 1013. The mass storage 1009 may include both fixed and removable media, such as other available mass storage technology. Bus 1018 may contain, for example, 32 address lines for addressing video memory 1014 or main memory 1015. The system bus 1018 also includes, for example, an n-bit data bus for transferring DATA between and among the components, such as processor 1013, main memory 1015, video memory 1014 and mass storage 1009, where "n" is, for example, 32 or 64. Alternatively, multiplex data/address lines may be used instead of separate data and address lines.

I/O device(s) 1019 may provide connections to peripheral devices, such as a printer, and may also provide a direct connection to a remote server computer systems via a telephone link or to the Internet via an ISP. I/O device(s) 1019 may also include a network interface device to provide a direct connection to a remote server computer systems via a direct network link to the Internet via a POP (point of presence). Such connection may be made using, for example, wireless techniques, including digital cellular telephone connection, Cellular Digital Packet Data (CDPD) connection, digital satellite data connection or the like. Examples of I/O devices include modems, sound and video devices, and specialized communication devices such as the aforementioned network interface. Computer programs are generally stored as code in mass storage 1019 until loaded into main memory 1015 for execution.

The processor 1013, in one embodiment, is a microprocessor manufactured by Motorola Inc. of Illinois, Intel Corporation of California, or Advanced Micro Devices of California. However, any other suitable single or multiple microprocessors or microcomputers may be utilized. Main memory 1015 is comprised of dynamic random access memory (DRAM). Video memory 1015 is a dual-ported video random access memory. One port of the video memory 1014 is coupled to video amplifier 1016. The video amplifier 1016 is used to drive the display 1017. Video amplifier 1016 is well known in the art and may be implemented by any suitable means. This circuitry converts pixel DATA stored in video memory 1014 to a raster signal suitable for use by display 1017. Display 1017 is a type of monitor suitable for displaying graphic images.

The computer system described above is for purposes of example only. The medical record generation and processing system 500 and 600 and the automated electronic medical record (eMR) learning method 700 may be implemented in any type of computer system or programming or processing environment. It is contemplated that the medical record generation and processing system 500 and 600 and the automated electronic medical record (eMR) learning method 700 might be run on a stand-alone computer system, such as the one described above. The medical record generation and processing system 500 and 600 and the automated electronic medical record (eMR) learning method 700 might also be run from a server computer systems system that can be accessed by a plurality of client computer systems interconnected over an intranet network. Finally, the medical record generation and processing system 500 and 600 and the automated electronic medical record (eMR) learning method 700 may be run from a server computer system that is accessible to clients over the Internet.

Although embodiments have been described in detail, it should be understood that various changes, substitutions, and alterations can be made hereto without departing from the spirit and scope of the invention as defined by the appended claims.

What is claimed is:

1. An method comprising:
receiving clinician note data in a first electronic system that includes patient medical-related data;
processing the clinician note data using a natural language data processor and medical record interpretation rules to automatically convert the clinician note data into an electronic medical record;
sending the electronic medical record to a second electronic system to allow review and modification of the converted clinician note data in the electronic medical record;
receiving feedback data in the first electronic system that indicates modifications to the converted clinician note data in the electronic medical record;
processing the feedback data to identify modifications to the converted clinician note data in the electronic medical record;
analyzing the modifications in the feedback data to determine whether to modify the medical record interpretation rules; and
modifying the medical record interpretation rules in accordance with at least a portion of the feedback data for use in processing subsequently received clinician note data if analysis of the modifications in the feedback data determines to modify the medical record interpretation rules.

2. The method of claim 1 further comprising:
using the natural language processor to process the clinician note data in accordance with the modified medical record interpretation rules.

3. The method of claim 1 wherein:
receiving feedback data comprises receiving feedback data from one or more data sources in a group consisting of: medical core measures feedback data and clinician feedback data; and
processing the feedback data to identify modifications to the converted clinician note data in the electronic medical record comprises at least one member of a group consisting of:
identifying modifications to the converted clinician note data in the electronic medical record as modifications from a medical core measures electronic system; and
identifying modifications to the converted clinician note data in the electronic medical record as modifications from a clinician medical note data entry and display system.

4. The method of claim 1 wherein:
receiving feedback data comprises receiving feedback data from multiple data sources in a group consisting of: medical coding feedback data, medical core measures feedback data, and clinician feedback data; and
processing the feedback data to identify modifications to the converted clinician note data in the electronic medical record comprises at least one member of a group consisting of:
identifying modifications to the converted clinician note data in the electronic medical record as modifications from a medical coding electronic system;
identifying modifications to the converted clinician note data in the electronic medical record as modifications from a medical core measures electronic system; and
identifying modifications to the converted clinician note data in the electronic medical record as modifications from a clinician medical note data entry and display system.

5. The method of claim 1 wherein processing the feedback data to identify modifications to the converted clinician note data in the electronic medical record comprises:
analyzing linguistics of the electronic medical record as modified to determine discrete contexts of portions of the electronic medical record;
analyzing statistics associated with the medical record interpretation rules; and
modifying the medical record interpretation rules in accordance with the linguistics and statistics analysis.

6. The method of claim 5 wherein analyzing statistics associated with the medical record interpretation rules comprises:
identifying variables that affect one or more of the medical record interpretation rules; and
modifying the medical record interpretation rules so that processing of subsequent clinician note data has a higher probability of accuracy and completeness relative to a probability of accuracy and completeness in processing of previous clinician note data.

7. The method of claim 1 wherein the medical record interpretation rules are customized in accordance to a member of a group consisting of: an individual clinician, a clinician's medical specialty, an individual patient, a patient's demographics, a medical facility, and a medical facility location.

8. The method of claim 1 further comprising:
identifying a medical record template corresponding to the clinician note data;
processing the clinician note data to standardize the clinician note data per predetermined data standards; and
operating the natural language processor to insert the clinician note data into the medical record template.

9. The method of claim 1 wherein the medical record interpretation rules comprise analytics associated with at least one member of the group of:
word count;
parts of speech;
medical ontologies; and
metadata associated with at least one of: a clinician and a medical facility.

10. An apparatus comprising:
one or more processors; and
a memory, coupled to the one or more processors, and storing code therein that is executable by the one or more processors for:
receiving clinician note data in a first electronic system that includes patient medical-related data;
processing the clinician note data using a natural language data processor and medical record interpretation rules to automatically convert the clinician note data into an electronic medical record;
sending the electronic medical record to a second electronic system to allow review and modification of the converted clinician note data in the electronic medical record;
receiving feedback data in the first electronic system that indicates modifications to the converted clinician note data in the electronic medical record;
processing the feedback data to identify modifications to the converted clinician note data in the electronic medical record;
analyzing the modifications in the feedback data to determine whether to modify the medical record interpretation rules; and
modifying the medical record interpretation rules in accordance with at least a portion of the feedback data for use in processing subsequently received clinician note data if analysis of the modifications in the feedback data determines to modify the medical record interpretation rules.

11. The apparatus of claim 10 wherein the code is further executable by the one or more processors for:
using the natural language processor to process the clinician note data in accordance with the modified medical record interpretation rules.

12. The apparatus of claim 10 wherein:
to receive feedback data, the code is further executable by the one or more processors for receiving feedback data from one or more data sources in a group consisting of: medical core measures feedback data and clinician feedback data; and
processing the feedback data to identify modifications to the converted clinician note data in the electronic medical record comprises at least one member of a group consisting of:
identifying modifications to the converted clinician note data in the electronic medical record as modifications from a medical core measures electronic system; and
identifying modifications to the converted clinician note data in the electronic medical record as modifications from a clinician medical note data entry and display system.

13. The apparatus of claim 10 wherein:
to receive feedback data, the code is further executable by the one or more processors for receiving feedback data from multiple data sources in a group consisting of: medical coding feedback data, medical core measures feedback data, and clinician feedback data; and
processing the feedback data to identify modifications to the converted clinician note data in the electronic medical record comprises at least one member of a group consisting of:
identifying modifications to the converted clinician note data in the electronic medical record as modifications from a medical coding electronic system;
identifying modifications to the converted clinician note data in the electronic medical record as modifications from a medical core measures electronic system; and
identifying modifications to the converted clinician note data in the electronic medical record as modifications from a clinician medical note data entry and display system.

14. The apparatus of claim 10 wherein to process the feedback data to identify modifications to the converted clinician note data in the electronic medical record, the code is further executable by the one or more processors for:
analyzing linguistics of the converted clinician note data in the electronic medical record as modified to determine discrete contexts of portions of the electronic medical record;
analyzing statistics associated with the medical record interpretation rules; and
modifying the medical record interpretation rules in accordance with the linguistics and statistics analysis.

15. The apparatus of claim 14 wherein to analyze statistics associated with the electronic medical record interpretation rules, the code is further executable by the one or more processors for:
identifying variables that affect one or more of the medical record interpretation rules; and
modifying the medical record interpretation rules so that processing of subsequent clinician note data has a higher probability of accuracy and completeness relative to a probability of accuracy and completeness in processing of previous clinician note data.

16. The apparatus of claim 10 wherein the medical record interpretation rules are customized in accordance to a member of a group consisting of: an individual clinician, a clinician's medical specialty, an individual patient, a patient's demographics, a medical facility, and a medical facility location.

17. The apparatus of claim 10 wherein the code is further executable by the one or more processors for:
identifying a medical record template corresponding to the clinician note data;
processing the clinician note data to standardize the clinician note data per predetermined data standards; and
operating the natural language processor to insert the clinician note data into the medical record template.

18. The apparatus of claim 10 wherein the medical record interpretation rules comprise analytics associated with at least one member of the group of:
word count;
parts of speech;
medical ontologies; and
metadata associated with at least one of: a clinician and a medical facility.

19. A tangible, non-transitory computer readable medium comprising code stored therein and executable by one or more processors for:
- receiving clinician note data in a first electronic system that includes patient medical-related data;
- processing the clinician note data using a natural language data processor and medical record interpretation rules to automatically convert the clinician note data into an electronic medical record;
- sending the electronic medical record to a second electronic system to allow review and modification of the converted clinician note data in the electronic medical record;
- receiving feedback data in the first electronic system that indicates modifications to the converted clinician note data in the electronic medical record;
- processing the feedback data to identify modifications to the converted clinician note data in the electronic medical record;
- analyzing the modifications in the feedback data to determine whether to modify the medical record interpretation rules; and
- modifying the medical record interpretation rules in accordance with at least a portion of the feedback data for use in processing subsequently received clinician note data if analysis of the modifications in the feedback data determines to modify the medical record interpretation rules.

20. The tangible, non-transitory computer readable medium of claim 19 wherein the code is further executable by the one or more processors for:
- using the natural language processor to process the clinician note data in accordance with the modified medical record interpretation rules.

21. The tangible, non-transitory computer readable medium of claim 19 wherein:
- to receive feedback data, the code is further executable by the one or more processors for receiving feedback data from one or more data sources in a group consisting of: medical core measures feedback data and clinician feedback data; and
- processing the feedback data to identify modifications to the converted clinician note data in the electronic medical record comprises at least one member of a group consisting of:
  - identifying modifications to the converted clinician note data in the electronic medical record as modifications from a medical core measures electronic system; and
  - identifying modifications to the converted clinician note data in the electronic medical record as modifications from a clinician medical note data entry and display system.

22. The tangible, non-transitory computer readable medium of claim 19 wherein:
- to receive feedback data, the code is further executable by the one or more processors for receiving feedback data from multiple data sources in a group consisting of: medical coding feedback data, medical core measures feedback data, and clinician feedback data; and
- processing the feedback data to identify modifications to the converted clinician note data in the electronic medical record comprises at least one member of a group consisting of:
  - identifying modifications to the converted clinician note data in the electronic medical record as modifications from a medical coding electronic system;
  - identifying modifications to the converted clinician note data in the electronic medical record as modifications from a medical core measures electronic system; and
  - identifying modifications to the converted clinician note data in the electronic medical record as modifications from a clinician medical note data entry and display system.

23. The tangible, non-transitory computer readable medium of claim 19 wherein to process the feedback data to identify modifications to the converted clinician note data in the electronic medical record, the code is further executable by the one or more processors for:
- analyzing linguistics of the converted clinician note data in the electronic medical record as modified to determine discrete contexts of portions of the electronic medical record;
- analyzing statistics associated with the medical record interpretation rules; and
- modifying the medical record interpretation rules in accordance with the linguistics and statistics analysis.

24. The tangible, non-transitory computer readable medium of claim 23 wherein to analyze statistics associated with the medical record interpretation rules, the code is further executable by the one or more processors for:
- identifying variables that affect one or more of the medical record interpretation rules; and
- modifying the medical record interpretation rules so that processing of subsequent clinician note data has a higher probability of accuracy and completeness relative to a probability of accuracy and completeness in processing of previous clinician note data.

25. The tangible, non-transitory computer readable medium of claim 19 wherein the medical record interpretation rules are customized in accordance to a member of a group consisting of: an individual clinician, a clinician's medical specialty, an individual patient, a patient's demographics, a medical facility, and a medical facility location.

26. The tangible, non-transitory computer readable medium of claim 19 wherein the code is further executable by the one or more processors for:
- identifying a medical record template corresponding to the clinician note data;
- processing the clinician note data to standardize the clinician note data per predetermined data standards; and
- operating the natural language processor to insert the clinician note data into the medical record template.

27. The tangible, non-transitory computer readable medium of claim 19 wherein the medical record interpretation rules comprise analytics associated with at least one member of the group of:
- word count;
- parts of speech;
- medical ontologies; and
- metadata associated with at least one of: a clinician and a medical facility.

* * * * *